United States Patent [19]

Tsunenaga et al.

[11] Patent Number: 5,137,875
[45] Date of Patent: Aug. 11, 1992

[54] HYALURONIC ACID-CONTAINING AQUEOUS SOLUTION OR AQUEOUS DISPERSION OF COLLAGEN

[75] Inventors: Makoto Tsunenaga; Naoki Tominaga, both of Yokohama; Toshio Nishiyama, Tokyo; Toru Yamashita, Yokohama; Mutsumi Fukuyama, Kawagoe; Teruo Miyata, Tokyo; Masayasu Furuse, Sagamihara, all of Japan

[73] Assignees: Shiseido Co., Ltd.; Koken Co., Ltd., both of Tokyo, Japan

[21] Appl. No.: 339,765

[22] Filed: Apr. 18, 1989

[30] Foreign Application Priority Data

Apr. 19, 1988 [JP] Japan .................. 63-95858

[51] Int. Cl.$^5$ .................. A61K 37/02; A61K 37/12; C08H 1/06
[52] U.S. Cl. .................. 514/21; 530/356
[58] Field of Search .................. 530/356; 514/21

[56] References Cited

U.S. PATENT DOCUMENTS

| | | | |
|---|---|---|---|
| 4,242,291 | 12/1980 | Hughes et al. | 264/1 |
| 4,424,208 | 1/1984 | Wallace et al. | 424/177 |
| 4,592,864 | 6/1986 | Miyata et al. | 530/356 |
| 4,801,539 | 1/1989 | Akasaka et al. | 435/101 |
| 4,803,075 | 2/1989 | Wallace et al. | 514/802 |
| 4,837,285 | 6/1989 | Berg et al. | 530/356 |

FOREIGN PATENT DOCUMENTS

| | | |
|---|---|---|
| 089145 | 9/1983 | European Pat. Off. |
| 196197 | 10/1986 | European Pat. Off. |
| 0268421 | 5/1988 | European Pat. Off. |
| 58-170796 | 10/1983 | Japan |
| 63-119772 | 5/1988 | Japan |

OTHER PUBLICATIONS

Kasai et al., "Platelet adhesion to collagen/mucopolysaccharide hybrid matrix," Jpn. J. Artif. Organs 12(1), 327–330 (1983).

*Primary Examiner*—Howard E. Schain
*Assistant Examiner*—Choon P. Koh
*Attorney, Agent, or Firm*—Varndell Legal Group

[57] ABSTRACT

A hyaluronic acid-containing aqueous solution or aqueous dispersion of collagen having a pH of from about 6.5 to about 8.0 and an osmolality of from about 230 to about 320 mOsm/kgH$_2$O. The aqueous solution or the aqueous dispersion of collagen is useful as an agent for correction and reparation of a depressed part of or a void in soft tissue of mammals.

14 Claims, 2 Drawing Sheets

HYALURONIC ACID-CONTAINING AQUEOUS SOLUTION OR AQUEOUS DISPERSION OF COLLAGEN

FIELD OF THE INVENTION

The present invention relates to a hyaluronic acid-containing aqueous solution or aqueous dispersion of collagen. The aqueous solution or the aqueous dispersion of the present invention can be used for internal injection into mammals. An injected solution of the present invention can be used for filling voids in defective tissues resulting from traffic accidents and operations without cutting out the surrounding tissues. In other words, the present invention can be used as an agent for correction and reparation of depressed parts of soft tissue underneath the skin of animals.

BACKGROUND OF THE INVENTION

Collagen is a protein which is abundant in skin, blood vessels, cornea, tendons, bones and teeth of animals, and which has a molecular weight of about 300,000. Collagen can be described as having a rod-like molecular structure of helical configuration consisting of three polypeptide chains, about 3,000 Å in length and about 15 Å in diameter.

Collagen is widely used in medical treatments. Purified collagen is used as local hemostatics, artificial skin, artificial eardrums, and contact lenses.

Collagen can also be injected into a living body for filling voids or depressions in defective tissues resulting from traffic accidents and operations, so that reparation of the tissues by fibroblasts is promoted. Conventionally, such an internally injected collagen comprises only collagen, such as an aqueous solution type (JP-B-62-37020) (the term "JP-B" as used herein means an examined Japanese Patent Publication), an aqueous dispersion of regenerated collagen fibers, and an aqueous dispersion of regenerated collagen fibers which have been crosslinked with a crosslinking agent (JP-A-58-170796, Japanese Patent Application No. 61-273156) (the term "JP-A" as used herein means an unexamined published Japanese Patent Application).

Specific examples include Koken Atelocollagen Implant (manufactured by Koken, Japan) as an aqueous solution type, Zyderm I and II (manufactured by Collagen Corp., U.S.A.) as a regenerated collagen fiber type, and Zyplast (manufactured by Collagen Corp., U.S.A.) as a crosslinked collagen type. The aqueous solution of collagen has an excellent fluidity through an injection needle, but it is easily absorbed into a living body. Thus, it has a problem with respect to antigenicity. Namely, an intracutaneous test observed 2 to 3% of subjects showing a response or reaction after injection, and a continued injection revealed additional 2 to 3% of subjects showing a response or reaction. Further, the required repetition of injection is necessary for maintaining an upheaval effect on skin. The upheaval effect of the skin can be described as the raising of the skin above the depression which is caused by injecting the aqueous solution of collagen into the depression underneath the skin. In other words, after injection of the aqueous solution of collagen into the depression, the skin is raised above the depression, so as to form a smooth level surface with the surrounding skin.

The crosslinked collagen can be made so that its absorption into a living body is reduced. Therefore, it has some advantages with respect to inhibition of antigenicity and maintenance of the upheaval effect on the skin. However, it has the problem that the addition of the residual crosslinking agent increases toxicity. Also, it has a fluidity inferior to that of the aqueous solution type and cannot be injected as smoothly as the aqueous solution type.

The properties of the regenerated fiber type collagen is positioned between those of the aqueous solution type and the crosslinked fiber type, and thus has both similar advantages and disadvantages. However, it is more easily absorbed into the body than the crosslinked collagen.

Hyaluronic acid is a component present in any part of a living body and is one of the substances called mucopolysaccharides. It is a very large, straight chain polymer having a molecular weight of from the hundreds thousands to millions. Hyaluronic acid consists of the chain of recurring disaccharide units in which N-acetylglucosamine and glucuronic acid are bonded together. Unlike the other mucopolysaccharides, it is free of a sulfate group and is believed to have the simplest structure of the mucopolysaccharides.

An aqueous solution of hyaluronic acid has a very characteristic viscoelastic property and a remarkably high water holding capacity, and it is in the form of viscous gel even in a dilute solution. Hyaluronic acid is one of the substrate components common to any connective tissues and hence has a function of holding water within the intercellular spaces.

It is known that hyaluronic acid forms a jelly-like matrix in the tissue to hold the cells and suppress the transfer of intercellular substances. This also protects against mechanical shocks and bacterial infection from the outside. The specific water holding capacity of hyaluronic acid is believed to be caused by the entanglement phenomenon that hyaluronic acid forms a continuous polymeric network in which individual molecules cannot be distinguished.

In the past, various attempts have been made to use these properties of hyaluronic acid for medical treatment. For example, hyaluronic acid has been used in treating agents for arthritic diseases, as vitreous replacements, and covering agents for skin wounds.

A specific aqueous collagen solution containing hyaluronic acid is described in Jinko Zoki (Japan J. Artificial Organs) 12(1), 327–220 (1983).

SUMMARY OF THE INVENTION

It is an object of the present invention to provide an aqueous solution or aqueous dispersion of collagen for internal injection, which can maintain the upheaval effect for a long period of time and has a further reduced antigenicity. As a result of extensive studies, it has been discovered by the present inventors that aqueous solutions or aqueous dispersions of collagen which contain a biocompatible and biological component, such as hyaluronic acid, rather than non-biological chemicals, can attain the objects of the present invention, and thus the present invention was achieved.

The present invention provides a hyaluronic acid-containing aqueous solution or aqueous dispersion of collagen having a pH of from about 6.5 to about 8.0 and an osmolality of from about 230 to about 320 mOsm/kg-$H_2O$.

BRIEF DESCRIPTION OF DRAWINGS

In FIGS. 1 and 2, (A) represents a 1% atelocollagen aqueous solution containing hyaluronic acid at 1%, (B) a 1% atelocollagen aqueous solution, (C) a 1% atelocollagen aqueous solution containing hyaluronic acid at 0.5%, (D) a 1% atelocollagen aqueous solution containing hyaluronic acid at 2%, and (E) a 2% atelocollagen aqueous solution containing hyaluronic acid at 2%.

DETAILED DESCRIPTION OF THE INVENTION

Figure 1:
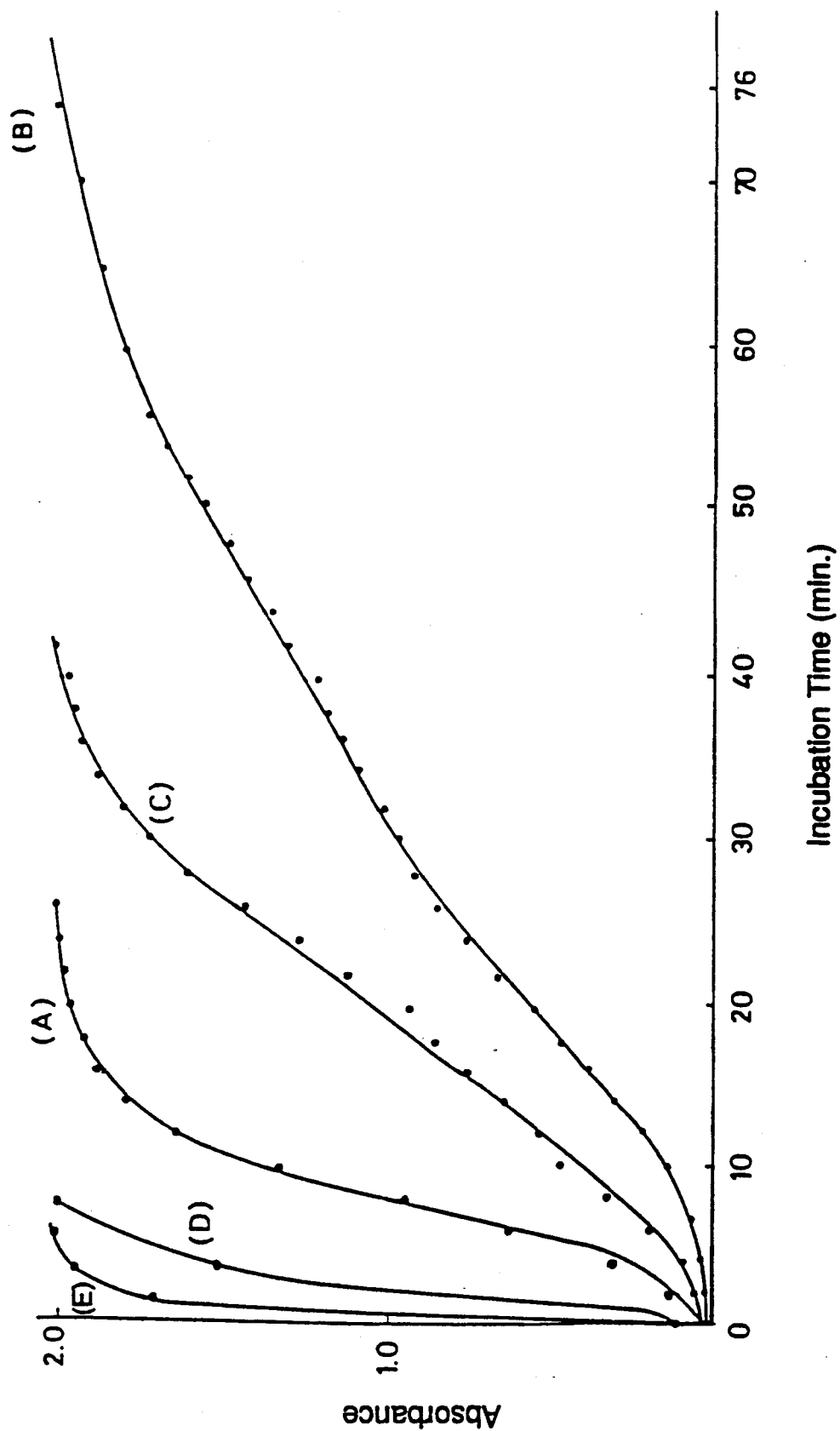
FIG. 1 shows a comparison of the rate of fiber formation under the biological conditions between the hyaluronic acid-containing aqueous solutions of atelocollagen and the aqueous solutions containing only atelocollagen, at various concentrations and proportions.

The hyaluronic acid-containing aqueous solution or aqueous dispersion of collagen according to the present invention is injected into human, animal, or mammal tissues having defective parts or portions void of tissue, which could have resulted from traffic accidents, operations, and other injuries. Therefore, it must have a pH and an osmolality which are consistent with the biological conditions. From this point of view, its pH and its osmolality are specified as described below. For adjusting the pH and the osmolality, phosphate buffers, such as $KH_2PO_4$-$K_2HPO_4$, $KH_2PO_4$-$Na_2HPO_4$, and $NaH_2PO_4$-$Na_2HPO_4$, and osmolality adjusting agents, such as glucose, can be used.

Depending on the nature of collagen used, either a hyaluronic acid-containing aqueous solution or aqueous dispersion of collagen is provided according to the present invention. When a water-soluble collagen is used as collagen material, a hyaluronic acid-containing aqueous solution of collagen is provided. When a regenerated collagen fiber or a crosslinked collagen after fiber regeneration is used as collagen material, a hyaluronic acid-containing aqueous dispersion of collagen is provided. In the present invention, a commercially available or known water soluble collagen can be used as the water-soluble collagen. For example, a water soluble collagen can be used which has been obtained as an acid-soluble collagen by extraction from various collagen containing materials by use of a dilute acid. The various collagen-containing materials can include, for example, skin, blood vessels, cornea, tendons, bones and teeth of animals. Alternatively, an insoluble collagen having intermolecular crosslinking can be made water soluble by treating it with a protease, such as pepsin.

In the hyaluronic acid-containing aqueous solution or aqueous dispersion of collagen of the present invention, the concentration and the proportion of hyaluronic acid and collagen can be varied within a wide range. The respective concentrations are preferably 0.01 to 10 wt % for hyaluronic acid and 0.01 to 10 wt % for collagen, more preferably 0.05 to 10 wt % for hyaluronic acid and 0.1 to 10 wt % for collagen, still more preferably 0.05 to 5 wt % for hyaluronic acid and 0.5 to 7 wt % for collagen, and most preferably 0.1 to 2 wt % for hyaluronic acid and 1 to 5 wt % for collagen.

By defining the respective concentrations of hyaluronic acid and collagen, as above, the effects of the present invention with respect to the upheaval effect of tissue depressions and antigenicity are more pronounced.

Because collagen for filling up the tissue defects or voids is injected into a living body, it should desirably have a low antigenicity. In this connection, it is preferred that the water-soluble collagen is atelocollagen, which is free of antigenic sites. The aforementioned commercially available Koken Atelocollagen Implant (manufactured by Koken, Japan) can suitably be used for this purpose.

By using atelocollagen as collagen, the hyaluronic acid-containing aqueous solution of collagen according to the present invention provides a mechanism whereby the rate of fiber formation can easily be adjusted. In addition, such a solution has an excellent upheaval effect and reduced antigenicity. Further, it has an excellent low temperature stability, when compared to an aqueous solution containing only atelocollagen.

In the present invention, the collagen is preferably regenerated collagen fibers. As regenerated collagen fibers, known regenerated collagen fibers (as described, for example, in JP-B-60-54288) can be used. For example, when the pH of an aqueous acid solution of collagen (pH, about 3), such as aqueous solution of hydrochloric acid, sulfuric acid and collagen, is increased to between 4.5 and 11 by addition of an appropriate aqueous alkali, such as an aqueous sodium hydroxide, collagen fibers are regenerated and precipitate.

The precipitates are collected and, if necessary, dried. Thus, collagen fibers are obtained. Alternatively, a concentrated buffer, such as a phosphate buffer, can be added to an aqueous acid solution of collagen, the mixture can be adjusted so as to become neutral at 5° C. or less, and then it can be warmed up to about body temperature. This causes the collagen to precipitate as fibers. The regenerated collagen fibers can be collected and, if necessary, dried.

The hyaluronic acid-containing aqueous dispersion of regenerated atelocollagen fibers are preferred from the viewpoint of antigenicity. The aforementioned Zyderm I and II by Collagen Corp. are commercially available and can be suitably used for this purpose.

In the present invention, the collagen is preferably in the form of crosslinked collagen. The hyaluronic acid-containing aqueous dispersion of crosslinked collagen is superior in upheaval effect and antigenicity, when compared to aqueous dispersions containing only crosslinked collagen.

As the crosslinked collagen, commercially available or known crosslinked collagen, such as that described in JP-A-58-10796 and Japanese Patent Application No. 61-273156, can be used.

The crosslinked collagen can be obtained by adding glutaraldehyde to an 1% aqueous dispersion of regenerated collagen fibers and stirring the mixture at room temperature overnight. The resulting crosslinked collagen can be collected, washed with water, and, if necessary, dried. The pH of the reaction medium is preferably neutral or alkaline. When hexamethylene-diisocyanate is used as a crosslinking agent, the above-mentioned regenerated collagen fibers prepared by adding an alkaline solution can be dispersed in an alcohol, such as methanol and ethanol, and then crosslinked with hexamethylene-diisocyanate.

As the crosslinked collagen, it is preferred to use crosslinked atelocollagen from the viewpoint of antigenicity.

Hyaluronic acid used in the present invention can be commercially prepared from chicken combs, eyeballs of mammals, and synovial liquids. It can also be obtained by culturing hyaluronic acid-producing microorganisms typified by streptococcus zooepidermicus.

The molecular weight of hyaluronic acid which can be used in the present invention is not restricted. Hyaluronic acid having a molecular weight of from the thousands to the millions can be used as needed. Examples of a hyaluronic acid having a high molecular weight are those having a molecular weight of about 3,000,000, Shiseido Biohyaluronic Acid (molecular weight, about 1,600,000 to about 2,000,000), and Shiseido Biohyaluronic Acid (molecular weight, about 650,000 to about 1,600,000), all of which can be used in the present invention.

If hyaluronic acid having a relatively low molecular weight, for example, of from the thousands to the hundreds of thousands, is used, fractions having the desired molecular weights of hyaluronic acid can be collected, as needed. Alternatively, hyaluronic acid having a high molecular weight may be converted for use by a physical method, such as by an autoclave treatment, to that having a low molecular weight.

The hyaluronic acid-containing aqueous solution or aqueous dispersion of collagen according to the present invention can be prepared by various methods.

For example, in the preparation of a hyaluronic acid-containing aqueous solution of collagen, an aqueous collagen solution can be mixed with an aqueous hyaluronic acid solution. In this case, the pH and osmolality of the mixture can be adjusted either by adjusting the pH and osmolality of each solution, prior to mixing. Alternatively, the pH and osmolality of the mixed solution can be adjusted after mixing. Moreover, hyaluronic acid and collagen may be dissolved into one solution, and then the pH and osmolality of the solution can be adjusted.

In a typical example of the preparation preparing a solution in accordance with the present invention, collagen is dissolved with stirring at an appropriate concentration in an acid solution having a pH of from 3.0 to 4.0, the pH and osmolality of the solution are adjusted to between 6.5 and 8.0 and between 230 to 320 mOsm/kgh$_2$O, respectively, by adding a pH and osmolality adjusting agents. A separate aqueous hyaluronic acid solution having an appropriate concentration hyaluronic acid is adjusted to have the same pH and the same osmolality as that of the collagen solution, and then the hyaluronic acid solution is mixed with the collagen solution.

The hyaluronic acid-containing aqueous dispersion of collagen according to the present invention can be prepared in manner similar to that of the preparation of the hyaluronic acid-containing aqueous solution of collagen.

The hyaluronic acid-containing aqueous solution or aqueous dispersion of collagen according to the present invention can be used as an agent for correction and reparation of depressed parts or void areas of soft tissue in mammals. The agent can be injected into defective tissue sites of men, animals and mammals, which have resulted from traffic accidents, operations, and other injuries. Various additives, as needed, can be added to the aqueous solution or the aqueous dispersion of the present invention. Additives can include an anesthetic, such as lidocaine. The amount of the additives can be suitably determined by those skilled in the art, provided that it conforms with the purpose of the additives and does not deteriorate the purpose and effect of the present invention. For example, the concentration of an anesthetic, such as lidocaine, can be from 0.1 to 1% (w/v) in the aqueous solution or aqueous dispersion of the present invention.

The hyaluronic acid-containing aqueous solution or aqueous dispersion of collagen according to the present invention can be injected with a syringe in an amount of from 0.01 to 1 ml per injection, depending on the size of the depression. The aqueous solution or dispersion of the present invention is injected into the defective or void tissue sites of men and animals. Such defective tissue can be caused by traffic accidents, operations, injuries, and the like, for example, depressions after operations, depressions caused by injuries, acne spots, depressions after treatment for Poland disease, and depressions by wrinkles.

When one injection is insufficient for healing, the number of injections is optionally increased and the injection is continued until appropriate healing is achieved (usually, once a day to once a month). The aqueous solution and the aqueous dispersion of the present invention can be intracutaneously injected and the aqueous dispersion of crosslinked collagen of the present invention can be subcutaneously injected.

The present invention will now be described by way of the following examples. The following examples are representative of the present invention and are not intended to limit the scope thereof in any way.

EXAMPLE 1

Koken Atelocollagen Implant (2% solution; pH 7.3; osmolality, 260 mOsm/kgH$_2$O) was prepared. 2 parts of by weight of powdered hyaluronic acid (Shiseido Biohyaluronic Acid; molecular weight, about 850,000 to about 1,600,000) was added to 98 parts by weight of 0.1M NaH$_2$PO$_4$-Na$_2$HPO$_4$ buffer (pH 7.3) in order to prepare an aqueous hyaluronic acid solution having a hyaluronic acid concentration of 2%, a pH of 7.3 and an osmolality of 260 mOsm/kgH$_2$O. Then, 50 parts by weight of the Atelocollagen Implant was added to 50 parts by weight of the aqueous hyaluronic acid solution. The mixture was thoroughly stirred to produce an aqueous atelocollagen solution containing atelocollagen and hyaluronic acid each at 1% concentration, and having a pH of 7.3 and an osmolality of 260 mOsm/kgH$_2$O.

EXAMPLE 2

A portion of the skin of a calf was washed thoroughly with purified water to remove any attached dirt. The calf skin thus obtained was disinfected with 70% ethanol, and all hairs on the uppermost surface of the skin were sliced off with a razor blade, so as not to leave any hair roots. The other side of the skin was also treated in the same manner for removing the fat layer. Thus, a piece of calf dermis was obtained under germ-free conditions.

This germ-free calf dermis was chopped and then washed with 5% aqueous NaCl solution. To 100 g of the chopped dermis, 4 liters of distilled water was added. The pH of the mixture was adjusted to 3.0 with 1N HCl. Then, 0.2 g of pepsin was added to the mixture. The mixture was treated at pH 3.0 for 3 days to solubilize the collagen, resulting in an atelocollagen solution. The pH of the solution was adjusted to 10 to deactivate the pepsin. The mixture was then purified by isoelectric point precipitation and filtration to yield germ-free and pyrogen-free atelocollagen. The resulting atelocollagen was dissolved in distilled water for injection, and the pH of the solution was adjusted to 3.0 with 1N HCl, so that the solution had an atelocollagen concentration of 6%. Then, 50 parts of weight of pyrogen-free 0.3M $KH_2PO_4$-$K_2HPO_4$ buffer (pH 7.5) was added to 100 parts by weight of the solution and thoroughly mixed. The resulting solution had an atelocollagen concentration of 4%, a pH of 7.3, and an osmolality of 280 $mOsm/kgH_2O$.

In the same manner, 96 parts by weight of 0.1M $KH_2PO_4$-$K_2HPO_4$ buffer (pH 7.3) was added to 4 parts of weight of powdered hyaluronic acid (molecular weight, about 1,600,000 to about 2,000,000) to produce a hyaluronic acid solution having a pH of 7.3 and an osmolality of 280 $mOsm/kgH_2O$. Then, 50 parts by weight of the hyaluronic acid solution was added to 50 parts by weight of the above atelocollagen solution and thoroughly mixed. The solution thus prepared had an atelocollagen concentration of 2%, a hyaluronic acid concentration of 2%, a pH of 7.3, and an osmolality of 280 $mOsm/kgH_2O$.

EXAMPLE 3

1 parts by weight of 1M $K_2HPO_4$-$KH_2PO_4$ buffer (pH 7.3) was added to 9 parts of weight of a 0.5% aqueous solution of acid-soluble collagen (Koken Cellgen I-AC) (pH 3) to produce a 0.45% aqueous solution of collagen having a pH of 7.3 and an osmolality of 230 $mOsm/kgH_2O$.

In the same manner, 99.55 parts by weight of 0.1M $K_2HPO_4$-$KH_2PO_4$ buffer (pH 7.3) was added to 0.45 parts of weight of powdered hyaluronic acid (molecular weight, about 3,000,000) to yield a 0.45% aqueous solution of hyaluronic acid having a pH of 7.3 and an osmolality of 230 $mOsm/kgH_2O$.

50 parts of weight of the above aqueous solution of acid-soluble collagen was added to 50 parts of weight of the above aqueous solution of hyaluronic acid to prepare a solution having an acid-soluble collagen concentration of 0.225%, a hyaluronic acid concentration of 0.225%, a pH of 7.3, and an osmolality of 230 $mOsm/kgH_2O$.

EXAMPLE 4

Aqueous dispersions were prepared in accordance with the method disclosed in JP-B-60-54288.

Collagen material and method:

Preparation of a bovine atelopeptide collagen solution:

A bovine skin was softened and then depilated by HCl treatment. The depilated skin was ground and dispersed in an amount of 8 to 11 g per liter of an aqueous HCl having a pH of 2. To the aqueous dispersion was added 0.1 wt % of pepsin based on the total amount of protein, and the mixture was treated at 15° to 20° C. for about 100 to 300 hours. Then, NaOH was added to raise the pH of the treating medium to about 10, thereby stopping the digestion. The deactivated (denatured) enzyme was removed from the reaction mixture by precipitation at a low pH. Thereafter, the resulting solution was cleaned and then concentrated by filtration and chromatography to prepare an aqueous dilute hydrochloric acid solution of bovine atelopeptide collagen (5 mg/ml; pH 3).

Preparation of regenerated collagen fiber:

0.02M $Na_2HPO_4$ at 18° C. was added to the above atelopeptide collagen solution to raise its pH to 7.4 for regenerating collagen fibers from the solution. The regenerated collagen fibers were separated from the supernatant, concentrated, and then homogenized using NaCl and $Na_2HPO_4$ to a physiological pH of 7.3 and ionic strength. The resulting dispersion contained collagen fibers at a concentration of 8% and had an osmolality of 300 $mOsm/kgH_2O$.

In the same manner, powdered hyaluronic acid (Shiseido Biohyaluronic Acid having molecular weight of about 1,600,000 to about 2,000,000) was used to prepare a 8% hyaluronic acid solution having a pH of 7.3 and an osmolality of 300 $mOsm/kgH_2O$. The solution was mixed with the above-prepared collagen fiber dispersion in equal amounts and stirred to produce a uniform dispersion. The dispersion thus produced contained 4% of each of hyaluronic acid and regenerated collagen fibers and had a pH of 7.3 and an osmolality of 300 $mOsm/kgH_2O$.

EXAMPLE 5

The solution prepared in accordance with EXAMPLE 2 and having an atelocollagen concentration of 2%, a hyaluronic acid concentration of 2%, a pH of 7.3, and an osmolality of 280 $mOsm/kgH_2O$ was heated to 37° C. and kept at this temperature for one hour to gel the solution. The resulting gel was stirred with a stirring rod to produce a hyaluronic acid-containing dispersion of the regenerated collagen fibers.

EXAMPLE 6

1 part by weight of atelocollagen was added to 99 parts by weight of 0.1M $K_2HPO_4$-$KH_2PO_4$ buffer (pH 7.3) to prepare a 1% collagen solution (pH 7.3). The solution was heated to 35° C. and kept at this temperature for 2 hours. The solution became a white turbid gel.

Ten ml of a physiological phosphate buffer containing glutaraldehyde and $K_2HPO_4$-$KH_2PO_4$ (pH, 7.4, 0.4 wt %) (glutaraldehyde content, 40 mg) was added to 10 g of the above-formed gel and reacted for one hour. The gel containing atelocollagen crosslinked with glutaraldehyde thus obtained was washed repeatedly to remove the aldehyde.

Then, the gel was subjected to centrifugation until the concentration of the glutaraldehyde-crosslinked atelocollagen was 150 mg/ml. An equal amount of a 1% solution of a hyaluronic acid (Shiseido Biohyaluronic acid; molecular weight, about 1,600,000 to about 2,000,000) prepared using a $K_2HPO_4$-$KH_2PO_4$ buffer (pH 7.3) was added to the centrifuged gel. The mixture was then stirred in a glass homogenizer for reducing the particle size of the cross-linked collagen to 50 to 100 μm. By this procedure, a mixed dispersion having a glutaraldehyde-crosslinked atelocollagen concentration of 7.5%, a hyaluronic acid concentration of 0.5%, a pH of 7.3, and an osmolality of 320 $mOsm/kgH_2O$ was obtained.

EXAMPLE 7

Koken Atelocollagen powder was dissolved in pyrogen-free aqueous hydrochloric acid solution (pH 3). The pH of the solution was adjusted to 7.0 by addition of an aqueous NaOH solution to precipitate regenerated collagen fibers, thus yielding an aqueous dispersion of the atelocollagen. In order to activate the amino group of the atelocollagen, an additional aqueous NaOH solution was added to the dispersion to raise its pH to 10.0. Then, the aqueous dispersion was dehydrated by ethanol displacement until the ethanol concentration as measured by an alcholometer exceeded 95 degrees. A dispersion of 1% collagen in ethanol was prepared. Hexamethylene-diisocyanate was added in an amount of 300 mg per gram of the collagen, on dry basis, to the dispersion and a reaction was carried out at 20° C. for 20 hours. After completion of the reaction, the resulting dispersion was washed with a large amount of ethanol to remove free hexamethylene-diisocyanate. Then, the ethanol in the dispersion was removed by water displacement and the dispersion was concentrated by centrifugation, to provide a collagen concentration of 80 mg/ml. Thereafter, the concentrate was treated in a glass homogenizer to reduce the particle size of the collagen to about 50 to about 100 μm. The crosslinking degree of the collagen contained in the dispersion as measured by the TNBS method (colorimetry using 2, 4, 6-trinitrobenzenesulfonic acid) was 65%. A phosphate buffer, 1M $Na_2HPO_4$-$NaH_2PO_4$, was added to the homogenized concentrate to prepare a dispersion of collagen in 0.1M $Na_2HPO_4$-$NaH_2PO_4$ (pH 7.0; collagen content, 70 mg/ml).

Separately, hyaluronic acid powder (Shiseido Biohyaluronic Acid; molecular weight, about 850,000 to about 1,600,000) was dissolved in a phosphate buffer, 0.1M $Na_2HPO_4$-$NaH_2PO_4$, to prepare a 7% hyaluronic acid solution (pH 7.0).

By mixing 50 parts of weight of the hyaluronic acid solution and 50 parts by weight of the dispersion of the collagen crosslinked using hexamethylene-diisocyanate, a dispersion was prepared which contained the crosslinked collagen at 3.5%, hyaluronic acid at 3.5% and which had a pH of 7.0 and an osmolality of 280 mOsm/$kgH_2O$.

EXAMPLE 8

A 6% collagen solution having a concentration of buffer ($Na_2HPO_4$-$NaH_2PO_4$ buffer) of 0.1M, a pH of 7.3, and an osmolality of 300 mOsm/$kgH_2O$ was prepared in accordance with EXAMPLE 2. Also, in accordance with EXAMPLE 2, 1%, 0.1% and 0.02% hyaluronic acid solutions, each having the same pH and the same osmolality as that of the 6% collagen solution, above, were prepared.

50 parts by weight of each of the three hyaluronic acid solutions were added to three separate solutions of 50 parts by weight of the 6% collagen solution, and the mixtures were thoroughly stirred.

The resulting solutions included a solution containing atelocollagen at 3% and hyaluronic acid at 0.5% and having a pH of 7.3 and an osmolality of 300 mOsm/kg-$H_2O$; a solution containing atelocollagen at 3% and hyaluronic acid at 0.05% and having a pH of 7.3 and an osmolality of 300 mOsm/$kgH_2O$; and a solution containing atelocollagen at 3% and hyaluronic acid at 0.01% and having a pH of 7.3 and an osmolality of 300 mOsm/$kgH_2O$.

Each of the solutions was subcutaneously injected into the depressed part of the skin of a mammal. As a result, the depressed part was repaired so as to be flat or, in other words, level with skin around the previously depressed part. This demonstrates that these solutions are suitable as internally injecting collagen solutions.

The advantages of the present invention are now described with respect to both of the hyaluronic acid-containing aqueous solution of collagen and the hyaluronic acid-containing aqueous dispersion of collagen. The hyaluronic acid-containing aqueous solution according to the present invention has the same fluidity as the conventional internally injecting aqueous collagen solution (as described, for example, in JP-B-62-37020 directed to an aqueous atelocollagen and its preparation). Thus, it has a fluidity sufficient for injection through an injection needle of small diameter. When the hyaluronic acid-containing aqueous solution according to the present invention is equilibrated with biological conditions, it regenerates collagen fibers. In addition, the presence of hyaluronic acid in the aqueous solution provides the advantages in physical properties over aqueous solutions containing only collagen. Namely, the rate of fiber formation is increased, the volume retention (water holding capacity) of the regenerated fibers is improved, and the elution rate of the regenerated collagen fibers is decreased. Furthermore, it provides the effect of inhibiting antigenicity. The rate of fiber formation and the volume retention are increased with the increase in the concentrations of aqueous collagen solution and hyaluronic acid. Therefore, different rates of fiber formation and different volume retentions can be obtained by changing each concentration and each proportion. Thus, the solutions having properties suited to various purposes can be prepared.

The above-mentioned advantages of the present invention are described of the case of internal injection. The aqueous solution of the present invention can be used for reparation or healing of a defective part of tissue or a void in the tissue of, for example, mammals. After the internal injection, the aqueous solution begins to regenerate fibers and the fibroblasts begin to migrate in the fibers. This provides an improved fit or meshing with the surrounding tissues. The injected aqueous solution of the present invention can retain a required volume for long period of time and has an increased intercellular water holding capacity. Thus, the upheaval effect at the defective part of tissue is improved. This makes it possible to decrease the number of injections for reparation or healing of the defective part of tissue. In addition, the delay of absorption the collagen eliminates the antigenicity and the toxicity problems associated with the use of a crosslinking agent.

In order to demonstrate the advantages of the presence of hyaluronic acid in the aqueous solution of the present invention, a hyaluronic acid-containing aqueous solution of collagen was compared with an aqueous collagen solution. Although the time required for forming fibers depends on the concentrations of collagen and hyaluronic acid, the presence of hyaluronic acid shortened the time lag before the beginning of the fiber formation and the rate of fiber formation was increased. Thus, hyaluronic acid is effective for inhibiting the absorption of collagen after injection into a living body of a mammal.

Also, a comparison was made, in which equal amounts of 2% collagen solution, as described in JP-B-62-37020, and 2% hyaluronic acid solution were mixed together, and the mixture was gelled to form collagen fibers. The gel was centrifuged, and the amounts of the separated supernatant and collagen in the supernatant were measured. Although these amounts also depend on the concentration and proportion of each of the collagen and hyaluronic acid, the amount of separated water (supernatant) was 75.5% based on the total volume for the 2% collagen solution, whereas it was 50% based on the total volume for the mixture of 2% collagen solution and 2% hyaluronic acid solution. Thus, the mixture of hyaluronic acid with collagen improved the volume retention (water holding capacity). The concentration of collagen in the supernatant was 0.34% for the 2% collagen solution and 0.18% for the mixture, which indicates that the collagen in the mixture is difficult to elute into the supernatant.

The mixture of the present invention was subcutaneously injected into a rat. After 3 months, an antibody reaction to collagen was investigated. As a result, it was found that an antibody reaction, although slight, was observed with the 2% collagen solution, while no antibody reaction was observed with the mixture of the present invention.

The above results can be summarized as follows.

When the hyaluronic acid-containing aqueous solution of collagen according to the present invention is injected internally, collagen fibers are rapidly regenerated and the injected solution maintains its volume and thus fills up or occupies the area of the defective parts of tissue for a long period of time. Therefore, the number of injections can be decreased. Because this aqueous solution has high fluidity, it can be injected smoothly through an injection needle. This aqueous solution does not bring about an antigenicity problem that can be caused with its absorption into a living body. Also, since collagen and hyaluronic acid are biogenic substances by nature, they are free from a toxicity problem. Thus, the hyaluronic acid-containing aqueous solution of collagen according to the present invention is quite suitable for internal injection. In addition, the rate of fiber formation depends on the concentrations of hyaluronic acid and collagen and, therefore, the rate of fiber formation can be varied by changing their respective concentrations and proportions, with the water holding capacity changes accordingly. Thus, the rate of fiber formation and water holding capacity can be selected or adjusted, so as to correspond with the reparation or healing needed. From the above, it is apparent that the aqueous solution of the present invention has diversity and advantages which conventional internal injecting aqueous atelocollagen solutions lack.

Also, the hyaluronic acid-containing aqueous solution of collagen according to the present invention does not precipitate fibers when it is stored at low temperature (for example, at 10° C. or less, in particular at 2° to 6° C.), but it precipitates fibers at the body temperature of mammals. Therefore, this aqueous solution can be stored for a long period of time and still be suitable for an internal injection. This low temperature stability is better than that of an aqueous solution containing only collagen.

As stated in the Background of the Invention, above, Jinko Zoki (Japan. J. Artificial Organs) 12(1), 327-330 (1983) describes an aqueous collagen solution containing hyaluronic acid (P. 327, right column). However, it does not refer to the pH of this aqueous solution, and the osmolality of this aqueous solution is not adjusted. The above-cited Jinko Zoki discloses (1) a matrix comprising collagen-hyaluronic acid strongly inhibits platelet adhesion, (2) the fibroblast growth on this matrix is good (in summary), and (3) hyaluronic acid hardly has an effect on the regeneration of collagen fibers (P. 328, left column, middle part).

However, (1) and (2) above have nothing to do with the advantages and effects of the present invention, and (3) is inconsistent with the present invention.

The hyaluronic acid-containing aqueous dispersion of the present invention is divided into a dispersion of regenerated collagen fibers and a dispersion of crosslinked collagen.

The dispersion of regenerated collagen fibers and crosslinked collagen both have improved upheaval effect and antigenicity as compared with the aqueous solution of collagen. The improvement is enhanced by using hyaluronic acid in combination therewith. (See Test Examples 5, 6 and 8 described hereinbelow.)

With the hyaluronic acid-containing aqueous dispersion of crosslinked collagen, the cytoxicity resulting from a crosslinking agent is further decreased in the present invention. (See Text Example 7 described hereinbelow.)

TEST EXAMPLE 1

A spectrophotometer cell was filled with the hyaluronic acid-containing aqueous solution of atelocollagen (1% hyaluronic acid and 1% atelocollagen) prepared in accordance with Example 1, and the content of the cell was examined after various procedures were carried out.

The atelocollagen solution in the cell was incubated in a water at 37° C. for 2 minutes, and then its absorbance at a wavelength of 400 nm was measured with a Hitachi Spectrophotometer Model 100-10. The incubation for 2 minutes and the measurement of absorbance were repeated until the absorbance became constant. In this manner the rate of fiber formation in the atelocollagen was measured. The result for this two component solution (hereinafter referred to as a mixed solution) is shown as (A) in FIG. 1.

In the same manner, the absorbance of a one-component solution of 1% atelocollagen (hereinafter referred to as a single solution) was measured, the result is shown as (B) in FIG. 1.

According to FIG. 1, it took about 26 minutes for the mixed solution to give a constant absorbance. On the other hand, it took about 76 minutes for the single solution, which was about 3 times longer than for the mixed solution. These results indicate that the rate of fiber formation in the mixed solution is about 3 times higher than that in the single solution.

Figure 2:
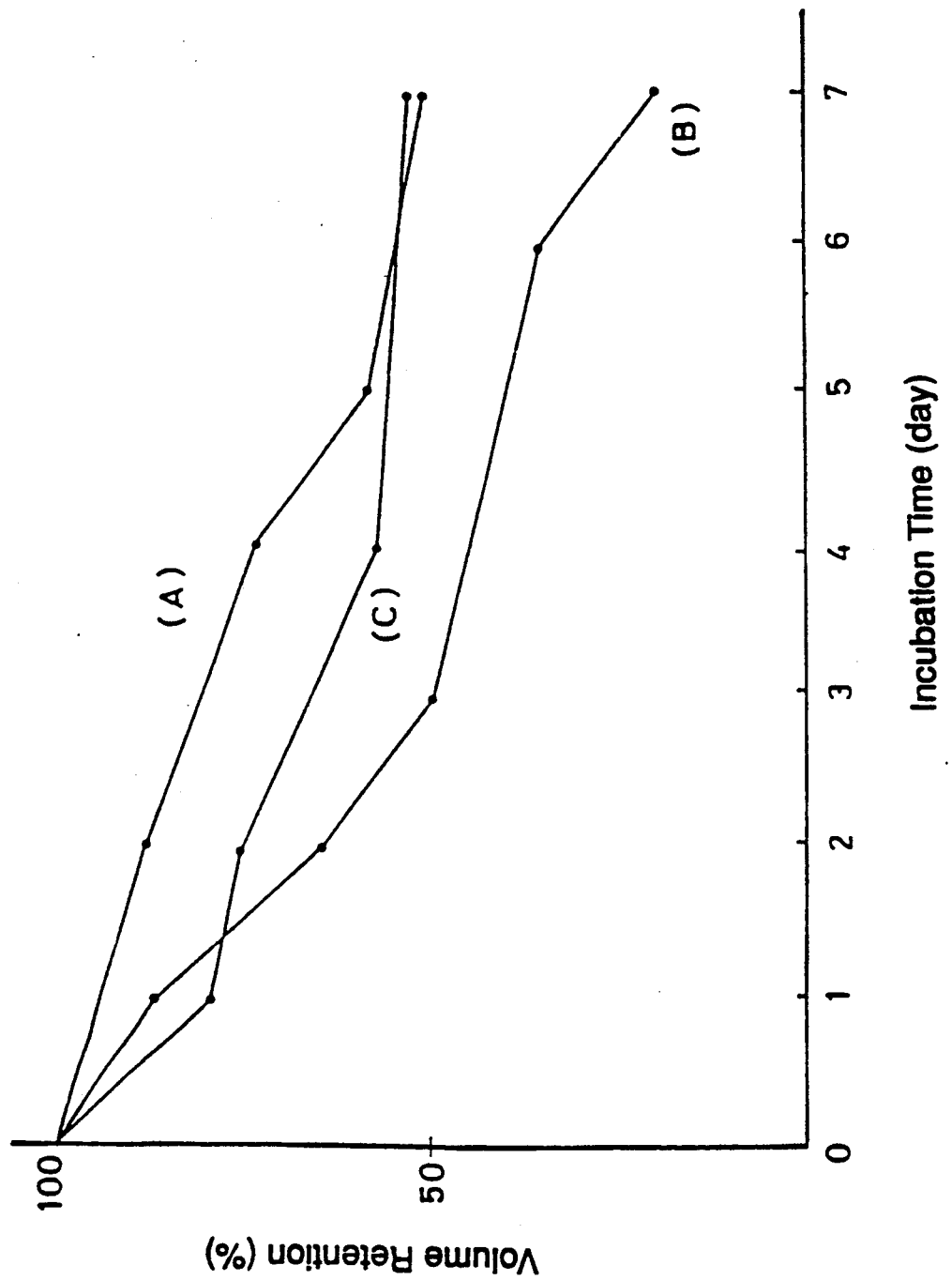
FIG. 2 shows a comparison of the volume retention as measured by centrifugation between the hyaluronic acid-containing aqueous solution of atelocollagen and the aqueous solution of atelocollagen containing only atelocollagen, at various concentration and proportions.

The hyaluronic acid-containing aqueous solution of atelocollagen prepared in accordance with Example 1 was charged in a centrifugal tube with a ground-in stopper, incubated at 37° C., and centrifuged at 10,000 rpm for 30 minutes every 24 hours. The water thus separated was taken for the decrement of volume for measuring the water retention. The results are shown in FIG. 2. In FIG. 2, (A) indicates the water retention of the mixed solution (1% atelocollagen and 1% hyaluronic acid).

In the same manner the water retention of the single solution of 1% atelocollagen was measured. The result is shown as (B) in FIG. 2.

When the mixed solution was compared with the single solution on the seventh day, the former retained 50% of the volume and the later only 24% of the volume. This result indicates that the addition of hyaluronic acid improves the water-holding capacity and thereby enhances the volume retention capacity.

In addition, the amount of collagen that had been eluted in the supernatant separated at the time of the measurement of volume retention was measured by measuring the amount of hydroxyproline in the supernatant. At a result, the amount of collagen in the supernatant was 36.5 mg for the mixed solution and 108.1 mg for the single solution, which corresponds to the elution rates of 9.3% and 26.1%, respectively. Thus, the elution rate of the mixed solution is about one-third of that of the single solution. This indicates that the mixed solution, when internally injected, not only promotes the upheaval effect but also is effective in reduction of antigenicity, because of the decrease in collagen absorption into the host body.

In brief, the hyaluronic acid-containing aqueous solution of atelocollagen of the present invention was capable of rapidly forming atelocollagen fibers, had enhanced volume retention capacity and reduced antigenicity and, therefore, was is a collagen solution suitable for internal injection.

TEST EXAMPLE 2

Following the procedures of Example 1, a hyaluronic acid-containing aqueous solution of atelocollagen containing atelocollagen at 1% and hyaluronic acid at 0.5% and having a pH of 7.3 and as osmolality of 240 mOsm/kgH$_2$O was prepared. The rate of fiber formation and the volume retention were measured in the same manner as in Test Example 1. Furthermore, the rate of fiber formation was measured also with the following solutions also prepared according to Example 1: a 1% atelocollagen aqueous solution containing hyaluronic acid at 2% and having a pH of 7.3 and an osmolality of 270 mOsm/kgH$_2$O, and a 2% atelocollagen aqueous solution containing hyaluronic acid at 2% and having a pH of 7.3 and an osmolality of 320 mOsm/kgH$_2$O.

The results are shown in FIGS. 1 and 2. In the Figures,(C) indicate the result for the 1% atelocollagen aqueous solution containing hyaluronic acid at 0.5%, (D) for the 1% atelocollagen aqueous solution containing hyaluronic acid at 2%, and (E) for the 2% atelocollagen aqueous solution containing hyaluronic acid at 2%.

TEST EXAMPLE 3

The 2% atelocollagen aqueous solution containing hyaluronic acid at 2% prepared according to Example 2 and an aqueous solution containing only atelocollagen at 2% each was subcutaneously injected to a rat. Three days after, the tissues were picked, and the injected part was stained with an anti-bovine collagen antibody.

Microscopic observation revealed that the hyaluronic acid-containing aqueous solution of atelocollagen penetrate and diffuse over an area 2.7 times as large as that with the aqueous solution containing only atelocollagen. This result indicates that the addition of hyaluronic acid is effective for enlarging the penetration areas.

In addition, the hyaluronic acid-containing aqueous solution of atelocollagen did not produce any fibers at a temperature lower than 4° C. but, when equilibrated with the biological conditions, it formed atelocollagen fibers. Thus, it is suitable as an internally injecting collagen solution.

TEST EXAMPLE 4

The hyaluronic acid-containing aqueous solution of acid-soluble collagen prepared in accordance with Example 3 did not produce any collagen fibers at a temperature lower than 4° C. but, when equilibrated with the biological conditions, it formed collagen fibers. Thus, it was suitable as an internally injecting aqueous collagen solution.

TEST EXAMPLE 5

Various aqueous solutions and aqueous dispersions of collagen as described hereinafter were used to confirm that effect of addition of hyaluronic acid on the reparation of the depressed part of rat skin. A portion of the skin was peeled off from the back of each of 40 rates with a scalpel, and the cut portion of the back was self-healed. The 40 rats having similar depressions in the healed portions were divided into Groups A through H each including 5 rats. Until the depression was maintained flat or level with the remainder of the rats' backs, an 0.03 ml of the aqueous solutions or the aqueous dispersions of collagen was intracutaneously injected to the rats in Groups A to D once a week and 0.05 of the aqueous dispersions of collagen was subcutaneously injected to the rats in Groups E to H once a week. When carrying out this procedure, the injection was discontinued when the depression was not maintained flat even after 6 injections. The aqueous solutions and the aqueous dispersions of collagen used are shown in Table 1, and the number of injection required for maintaining the depression flat is shown in Table 2.

TABLE 1

| Group | Kind of Collagen (Concentration) | Concentration of Hyaluronic Acid | Remarks |
|---|---|---|---|
| A | Atelocollagen (1%) | 1% | Example 1 |
| B | Atelocollagen (1%) | 0 | |
| C | Regenerated Atelocollagen Fiber (4%) | 4% | Example 4 |
| D | Regenerated Atelocollagen Fiber (4%) | 0 | |
| E | Glutaraldehyde-Crosslinked Collagen (7.5%) | 0.5% | Example 6 |
| F | Glutaraldehyde-Crosslinked Collagen (7.5%) | 0 | |
| G | Hexamethylene-diisocyanate-Crosslinked Collagen (3.5%) | 3.5% | Example 7 |
| H | Hexamethylene-diisocyanate-Crosslinked Collagen (3.5%) | 0 | |

TABLE 2

| | A | B | C | D | E | F | G | H |
|---|---|---|---|---|---|---|---|---|
| 1 | 3 | 5 | 1 | 2 | 1 | 1 | 1 | 1 |
| 2 | 5 | 6 | 1 | 3 | 1 | 1 | 1 | 2 |
| 3 | 2 | 6 | 2 | 3 | 1 | 1 | 1 | 1 |
| 4 | 2 | 5 | 1 | 5 | 1 | 1 | 1 | 1 |
| 5 | 1 | 6 | 1 | 2 | 1 | 1 | 1 | 1 |
| Average | 2.6 | 5.6 | 1.2 | 3.0 | 1.0 | 1.0 | 1.0 | 1.2 |

It is apparent from the results in Table 2 that with the aqueous solutions of atelocollagen and the aqueous dispersions of regenerated atelocollagen containing of hyaluronic acid, it is possible to reduce the number of injections required for treatment. With the crosslinked collagen, most of the depressions were maintained in the state of upheaval for 10 days by only about one injection. In this case, in order to confirm the effect of the addition of hyaluronic acid, further observations were made. In these observations, the upheaval disappeared on the 16th week in Group F and on the 15th week in Group H, while in Groups E and G with the addition of hyaluronic acid to the treating dispersions, the upheaval was maintained even after 20 weeks.

TEST EXAMPLE 6

The decomposition rate of the aqueous solutions and the aqueous dispersions of collagen used in Text Example 5 were measured by using a collagenase of microbial origin to evaluate the volume retention in a living body. The results are shown in Table 3.

TABLE 3

|   | Hyaluronic Acid | Decomposition (%) |
|---|---|---|
| A | + | 95.5 |
| B |   | 100 |
| C | + | 90.9 |
| D |   | 100 |
| E | + | 10.5 |
| F |   | 15.3 |
| G | + | 14.5 |
| H |   | 20.5 |

"+" indicates the treating solution or dispersion contained hyaluronic acid.

The results in Table 3 indicate that the addition of hyaluronic acid increases the stability to the collagenase and enhances the volume retention in a living body.

TEST EXAMPLE 7

A culture test in vitro for human fibroblasts was conducted, in which various collagen liquids were coated on a culture dish and air dried. Then, $1 \times 10^5$ fibroblasts were seeded on the dried collagen and cultured for 7 days, and the number of cells was counted and their shapes were observed. A culture dish on which no collagen was coated was also tested as control. The kind of atelocollagen and the results are shown in Table 4.

TABLE 4

| Kind of Atelocollagen | Number of Cells | Shape of Cell |
|---|---|---|
| Aqueous dispersion containing glutaraldehyde-crosslinked atelocollagen at 7.5% and hyaluronic acid at 0.5% | $5 \times 10^5$ | Normal |
| Aqueous dispersion containing glutaraldehyde-crosslinked atelocollagen at 7.5% | $2.2 \times 10^5$ | Very abnormal |
| 7.5% uncrosslinked atelocollagen | $5.3 \times 10^5$ | Normal |
| No collagen | $5.0 \times 10^5$ | Normal |

From the results in Table 4, it has been confirmed that the addition of hyaluronic acid inhibits the toxicity of the crosslinked atelocollagen.

TEST EXAMPLE 8

It is known that, when bovine collagen is chemically crosslinked, its antigenicity is decreased to some extent. In this test example, it will be confirmed that the antigenicity of the bovine collagen is further decreased by using hyaluronic acid and collagen in combination in accordance with the present invention.

For each of the formulations of TEST EXAMPLE 5, 20 guinea pigs were provided, and the guinea pigs were subjected to sensitized induction with each formulation. In order to enhance the sensitivity of guinea pig, an appropriate adjuvant was used. Three weeks after, the formulation used in sensitized induction was injected into the guinea pigs to induce sensitization.

After 24 hours, the number of guinea pigs showing erythema in the injected part was counted. The results are shown in Table 5.

TABLE 5

|   | A | B | C | D | E | F | G | H |
|---|---|---|---|---|---|---|---|---|
| Number of guinea pigs used in injection test | 20 | 20 | 20 | 20 | 20 | 20 | 20 | 20 |
| Number of guinea pigs showing erythema | 4 | 12 | 6 | 11 | 3 | 5 | 2 | 5 |

It is apparent from the results in Table 5 that the addition of hyaluronic acid to the collagen solutions or the collagen dispersions decreases the antigenicity.

What is claimed is:

1. An injectable aqueous dispersion for reparation of defective tissues in mammals having decreased absorption and increased volume retention, a pH of from about 6.5 to 8.0 and an osmolality of from about 230 to about 320 mOsm/kgH$_2$O and comprising 0.01 to 10 wt % of hyaluronic acid and 0.01 to 10 wt % of substantially non-porous collagen having a particle size of about 50 to about 100 microns.

2. The injectable aqueous dispersion of claim 1 wherein said collagen is selected from a group consisting of atelocollagen and regenerated atelocollagen.

3. A method of repairing voids in tissues of mammals comprising injecting the injectable aqueous dispersion of claim 1 into said voids.

4. An aqueous solution comprising a water-soluble collagen and hyaluronic acid and having a pH of from about 6.5 to about 8.0 and an osmolality of from about 230 to about 320 mOsm/kgH$_2$O.

5. An aqueous solution of claim 4, wherein water-soluble collagen is water-soluble atelocollagen.

6. The aqueous solution of claim 4, wherein the water-soluble collagen is derived from acid-soluble collagen.

7. The aqueous solution of claim 4, wherein hyaluronic acid content is from 0.01 to 10 wt % and water-soluble collagen content is from 0.01 to 10 wt %.

8. The aqueous dispersion of claim 5, wherein hyaluronic acid content is from 0.01 to 10 wt % and water-soluble collagen content is from 0.01 to 10 wt %.

9. A method of repairing voids in tissues of mammals comprising of injecting the aqueous solution of claim 4 into said voids.

10. An injectable aqueous solution comprising a water-soluble collagen and hyaluronic acid and having a pH of from about 6.5 to about 8.0 and an osmolality of from about 230 to about 320 mOsm/KgH$_2$O for reparation of defective tissues in mammals having decreased absorption and increased volume retention and precipitating collagen fibers after injection.

11. The injectable aqueous solution of claim 10, wherein hyaluronic acid content is from 0.01 to 10 wt % and water-soluble collagen content is from 0.01 to 10 wt %.

12. The injectable aqueous solution of claim 11, wherein collagen fiber formulation rate is adjusted by changing respective concentrations of hyaluronic acid and water-soluble collagen.

13. The aqueous solution of claim 10, wherein said water-soluble collagen in said injectable aqueous solution remains water-soluble at low temperatures but precipitates at a body temperature of said mammals.

14. The injectable aqueous solution of claim 13, wherein said low temperatures are 10° C. or less.

* * * * *